(12) United States Patent
Bosmans et al.

(10) Patent No.: US 6,509,339 B2
(45) Date of Patent: Jan. 21, 2003

(54) N-SUBSTITUTED 4-((4'-AMINOBENZOYL)-OXYMETHYL)-PIPERIDINES HAVING GASTRIC PROKINETIC PROPERTIES

(75) Inventors: Jean-Paul René Marie Bosmans, Rijkevorsel (BE); Christopher John Love, Deurne (BE); Marc Gustaaf Celine Verdonck, Lille (BE); Joannes Adrianus Jacobus Schuurkes, Beerse (BE)

(73) Assignee: Janssen Pharmaceutica N.V. (BE)

( * ) Notice: Subject to any disclaimer, the term of this patent is extended or adjusted under 35 U.S.C. 154(b) by 0 days.

(21) Appl. No.: 09/933,094

(22) Filed: Aug. 20, 2001

(65) Prior Publication Data

US 2002/0042430 A1 Apr. 11, 2002

Related U.S. Application Data

(63) Continuation of application No. 09/125,901, filed as application No. PCT/EP97/00585 on Feb. 7, 1997, now Pat. No. 6,291,481.

(30) Foreign Application Priority Data

Feb. 29, 1996 (EP) ............................................. 96200525

(51) Int. Cl.[7] .................... C07D 405/14; A61K 31/454; A61K 31/501

(52) U.S. Cl. .................. 514/248; 514/255.05; 514/256; 514/266.22; 514/269; 514/252.03; 514/318; 514/320; 514/321; 514/322; 514/326; 514/331; 544/238; 544/237; 544/287; 544/298; 544/321; 544/333; 544/336; 544/405; 546/194; 546/196; 546/197; 546/210

(58) Field of Search .................. 546/196, 197, 546/210, 235, 194; 514/320, 318, 321, 322, 331, 326, 248, 252.03, 266, 22, 256, 269, 255.05; 544/237–238, 287, 298, 321, 333, 336, 405

(56) References Cited

U.S. PATENT DOCUMENTS

| | | | | |
|---|---|---|---|---|
| 5,705,509 A | * | 1/1998 | Gaster et al. | ............... 514/322 |
| 6,291,481 B1 | * | 9/2001 | Bosmans et al. | ........... 514/320 |

FOREIGN PATENT DOCUMENTS

| | | |
|---|---|---|
| WO | WO93/03725 A1 | 3/1993 |
| WO | WO93/05038 A1 | 3/1993 |
| WO | WO93/16072 A1 | 8/1993 |
| WO | WO94/05654 A1 | 3/1994 |
| WO | WO94/08994 A1 | 4/1994 |
| WO | WO94/08995 A1 | 4/1994 |
| WO | 94/10174 * | 5/1994 |
| WO | WO94/29298 A1 | 12/1994 |
| WO | WO96/28424 A1 | 9/1996 |
| WO | 96/33186 * | 10/1996 |

OTHER PUBLICATIONS

Clark et al., Bioorg.Med. Chem.Lett. vol. 4,pp. 2481–2484 (1994).*
Bioorg. Med. Chem. Lett., vol. 6, No. 3, pp. 263–266 1996; Fancelli, D. et al., "Serotoninergic 5–HT$_3$ and 5–HT$_4$ Receptor Activities of Dihydrobenzofuran Carboxylic Acid Derivatives".
J. Med. Chem. (1993), 36(25), pp. 4121–4123; Gaster, I.M. et al., "(1–Butyl–4–piperidinyl)methyl 8–Amino–7–chloro–1,4–benzodioxane–5–carboxylate Hydrochloride: A Highly Potent and Selective 5–HT4 Receptor Antagonist Derived from Metoclopramide".
J. Am. Chem. Soc., (1989), vol. 111, No. 23, pp. 8742–8744; Ben–David, Y. et al.: "Chelate–Assisted, Pd–Catalyzed Efficient Carbonylation of Aryl Chlorides".

* cited by examiner

*Primary Examiner*—Emily Bernhardt

(57) ABSTRACT

This invention concerns the compounds of formula

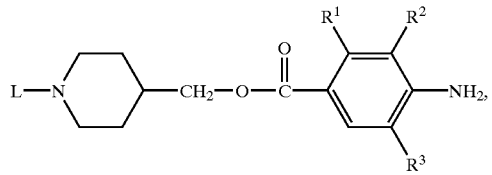

(I)

the N-oxide forms, the pharmaceutically acceptable acid addition salts and the stereochemically isomeric forms thereof, wherein $R^1$ is $C_{1-6}$alkyloxy, $C_{2-6}$alkenyloxy or $C_{2-6}$alkynyloxy; $R^2$ is hydrogen or $C_{1-6}$alkyloxy, or when taken together $R^1$ and $R^2$ may form a bivalent radical of formula wherein in said bivalent radicals one or two hydrogen atoms may be substituted with $C_{1-6}$alkyl, $R^3$ is hydrogen or halo; L is $C_{3-6}$cycloalkyl, $C_{5-6}$cycloalkanone, $C_{2-6}$alkenyl optionally substituted with aryl, or L is a radical of formula -Alk-$R^4$, -Alk-$NR^5R^6$, 1-$R^6$-4-piperidinyl, Alk-X—$R^7$, -Alk-Y—C(=O)—$R^9$, or -Alk-Y—C(=O)—$NR^{11}R^{12}$ wherein each Alk is $C_{1-12}$alkanediyl; $R^4$ is hydrogen, $C_{1-6}$alkylsulfonylamino, $C_{3-6}$cycloalkyl, $C_{5-6}$cycloalkanone, Ar-, di(Ar)methyl, Ar-oxy- or Het[1]; $R^5$ is hydrogen or $C_{1-6}$alkyl; $R^6$ is Het[2]; $R^7$ is hydrogen, $C_{1-6}$alkyl, hydroxy $C_{1-6}$alkyl, $C_{3-6}$cycloalkyl, Ar or Het[2]; X is O, S, $SO_2$ or $NR^8$; said $R^8$ being hydrogen, $C_{1-6}$alkyl or Ar; $R^9$ is hydrogen, $C_{1-6}$alkyl, $C_{3-6}$cycloalkyl, Ar, Ar$C_{1-6}$alkyl, di(Ar)methyl, $C_{1-6}$alkyloxy or hydroxy; Y is $NR^{10}$ or a direct bond; said $R^{10}$ being hydrogen, $C_{1-6}$alkyl or Ar; $R^{11}$ and $R^{12}$ each independently are hydrogen, $C_{1-6}$alkyl, $C_{3-6}$cycloalkyl, Ar or Ar$C_{1-6}$alkyl, or $R^{11}$ and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl. Processes for preparing said products, formulations comprising said products and their use as a medicine are disclosed, in particular for treating conditions which are related to impairment of gastric emptying.

6 Claims, No Drawings

N-SUBSTITUTED 4-((4'-AMINOBENZOYL)-OXYMETHYL)-PIPERIDINES HAVING GASTRIC PROKINETIC PROPERTIES

This application is a continuation application of U.S. Ser. No. 09/125,901, filed Aug. 27, 1998, now U.S. Pat. No. 6,291,481, which application is the national stage of application No. PCT/EP97/00585, filed Feb. 7, 1997.

The present invention is concerned with novel compounds of formula (I) having superior gastrokinetic properties. The invention further relates to methods for preparing such novel compounds, pharmaceutical compositions comprising said novel compounds as well as the use as a medicine of said compounds.

Compounds structurally related to the present novel compounds are disclosed in the prior art. WO 93/05038, published on Mar. 18, 1993, discloses (1-butyl-4-piperidinyl)methyl 8-amino-7-chloro-1,4-benzodioxan-5-carboxylate having 5 $HT_4$ receptor antagonistic activity. WO 93/16072, published on Aug. 19, 1993 discloses (1-butyl-4-piperidinyl)methyl-5-amino-6-chloro-3,4-dihydro-2H-1-benzopyran-8-carboxylate hydrochloride having 5 $HT_4$ receptor antagonistic activity. Recently, Fancelli D. et al., *Bioorganic & Medicinal Chem. Lett.*, 6:263–266, 1996, and WO-96/33186, published on Oct. 24, 1996, disclose (1-butyl-4-piperidinyl)methyl-4-amino-5-chloro-2,3-dihydrobenzo[b]furan-7-carboxylate hydrochloride having 5 $HT_4$ receptor agonistic activity.

WO 94/29298, published on Dec. 22, 1994 discloses 8-amino-7-chloro-1,4-benzodioxan-5-(1-butyl-4-piperidinyl)carboxylate having 5 $HT_4$ receptor antagonistic activity. WO 94/10174, published on May 11, 1994 discloses 5-(1-(3-pyridylmethyl)-4-piperidinyl)methyl-8-amino-7-chloro-1,4-benzo-dioxancarboxylate, [1-(2-carboethoxyethyl)-4-piperidinyl]methyl-8-amino-7-chloro-1,4-benzodioxan-5-carboxylate, [1-(3-hydroxybutyl)-4-piperidinyl]methyl-8-amino-7-chloro-1,4-benzodioxan-5-carboxylate having 5 $HT_4$ receptor antagonistic activity. Also, WO-96/28424, published on Sep. 19, 1996, discloses disubstituted 1,4-piperidine esters and amides having 5 $HT_4$ receptor antagonistic activity.

The cited prior art documents disclose compounds having 5 $HT_4$ receptor antagonistic activity and may generally be used in the treatment or prophylaxis of gastrointestinal disorders, cardiovascular disorders and CNS disorders. In particular, these compounds are thought to be useful in the treatment of irritable bowel syndrome (IBS), especially the diarrhoea aspects of IBS by blocking the ability of 5-HT to stimulate gut motility.

The problem which this invention sets out to solve is to provide gastric prokinetic compounds, i.e. the actual stimulation of gastric motility.

It is generally believed that gastric prokinetic activity is correlated with 5 $HT_4$ receptor agonist activity, i.e. the opposite of 5 $HT_4$ antagonist activity, (King F. D. et al., *J. Med. Chem.*, 36:683–689, 1993 and Langlois M. et al., *Bioorganic & Medicinal Chem. Lett.*, 4:1433–1436, 1994).

Hence it was surprising to find that the present compounds of formula (I) show gastric prokinetic activity.

In one embodiment, this invention concerns the use of compounds of formula

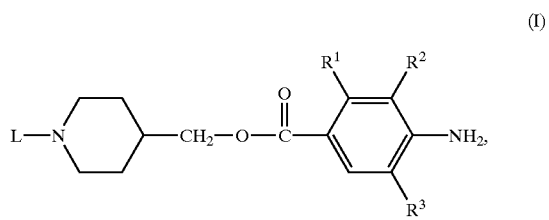

the N-oxide forms, the pharmaceutically acceptable acid addition salts and the stereochemically isomeric forms thereof, wherein $R^1$ is $C_{1-6}$alkyloxy, $C_{2-6}$alkenyloxy or $C_{2-6}$alkynyloxy;
$R^2$ is hydrogen or $C_{1-6}$alkyloxy,
or when taken together $R^1$ and $R^2$ may form a bivalent radical of formula

| —O—CH$_2$—O— | (a-1), |
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), | wherein in said bivalent radicals one or two hydrogen atoms may be substituted with $C_{1-6}$alkyl;
$R^3$ is hydrogen or halo;
L is $C_{3-6}$cycloalkyl, $C_{5-6}$cycloalkanone, $C_{2-6}$alkenyl optionally substituted with Ar, or L is a radical of formula

| —Alk—$R^4$, | (b-1) |
| —Alk—$NR^5R^6$, | (b-2) |

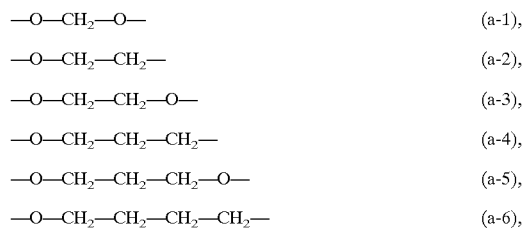

| —Alk—X—$R^7$, | (b-4) |
| —Alk—Y—C(=O)—$R^9$, and | (b-5) |
| —Alk—Y—C(=O)—$NR^{11}R^{12}$, | (b-6) | wherein
Alk is $C_{1-12}$alkanediyl;
$R^4$ is hydrogen, $C_{1-6}$alkylsulfonylamino, $C_{3-6}$cycloalkyl, $C_{5-6}$cycloalkanone, Ar-, di(Ar)methyl, Ar-oxy- or $Het^1$;
$R^5$ is hydrogen or $C_{1-6}$alkyl;
$R^6$ is $Het^2$;
$R^7$ is hydrogen, $C_{1-6}$alkyl, hydroxy$C_{1-6}$alkyl, $C_{3-6}$cycloalkyl, Ar or $Het^2$;
X is O, S, $SO_2$ or $NR^8$; said $R^8$ being hydrogen, $C_{1-6}$alkyl or Ar,
$R^9$ is hydrogen, $C_{1-6}$alkyl, $C_{3-6}$cycloalkyl, Ar, Ar$C_{1-6}$alkyl, di(Ar)methyl, $C_{1-6}$alkyloxy or hydroxy;
Y is $NR^{10}$ or a direct bond; said $R^{10}$ being hydrogen, $C_{1-6}$alkyl or Ar;
$R^{11}$ and $R^{12}$ each independently are hydrogen, $C_{1-6}$alkyl, $C_{3-6}$cycloalkyl, Ar or Ar$C_{1-6}$alkyl, or $R^{11}$ and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl;

each Ar being unsubstituted phenyl or phenyl substituted with 1, 2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and Het¹ and Het² each independently are selected from furan; furan substituted with $C_{1-6}$alkyl or halo; tetrahydrofuran; a tetrahydrofuran substituted with $C_{1-6}$alkyl; a dioxolane; a dioxolane substituted with $C_{1-6}$alkyl, a dioxane; a dioxane substituted with $C_{1-6}$alkyl; tetrahydropyran; a tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one or two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

Het¹ can also be a radical of formula

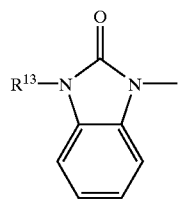
(c-1)

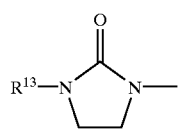
(c-2)

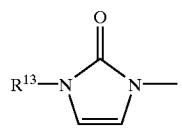
(c-3)

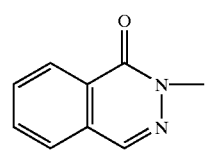
(c-4)

Het¹ and Het² each independently can also be selected from the radicals of formula

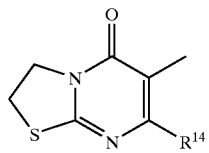
(d-1)

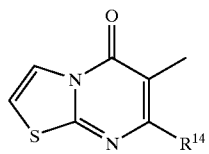
(d-2)

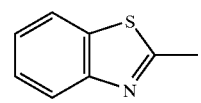
(d-3)

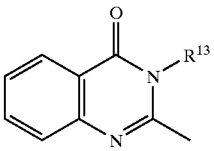
(d-4)

$R^{13}$ and $R^{14}$ each independently are hydrogen or $C_{1-4}$alkyl;

with the proviso that L is other than n-butyl when $R^1$ and $R^2$ are taken together to form a bivalent radical of formula (a-2);

for the manufacture of a medicine for treating conditions involving a decreased motility of the stomach.

In another embodiment, this invention concerns novel compounds of formula (I')

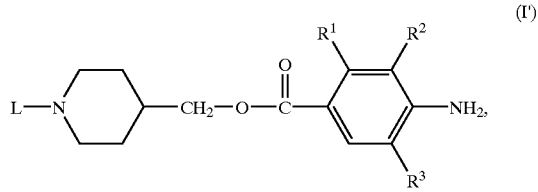
(I')

the N-oxide forms, the pharmaceutically acceptable acid addition salts and the stereochemically isomeric forms thereof, wherein $R^1$ is $C_{1-6}$alkyloxy, $C_{2-6}$alkenyloxy or $C_{2-6}$alkynyloxy;

$R^2$ is hydrogen or $C_{1-6}$alkyloxy, or when taken together $R^1$ and $R^2$ may form a bivalent radical of formula —O—CH$_2$—O— (a-1), —O—CH$_2$—CH$_2$— (a-2), —O—CH$_2$—CH$_2$—O— (a-3), —O—CH$_2$—CH$_2$—CH$_2$— (a-4), —O—CH$_2$—CH$_2$—CH$_2$—O— (a-5), —O—CH$_2$—CH$_2$—CH$_2$—CH$_2$— (a-6), wherein in said bivalent radicals one or two hydrogen atoms may be substituted with $C_{1-6}$alkyl;

$R^3$ is hydrogen or halo;

L is $C_{3-6}$cycloalkyl, $C_{5-6}$cycloalkanone, $C_{2-6}$alkenyl optionally substituted with Ar, or L is a radical of formula

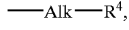 (b-1)

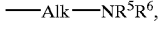 (b-2)

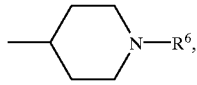 (b-3)

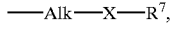 (b-4)

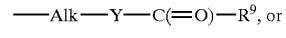 (b-5)

 (b-6)

wherein

Alk is $C_{1-12}$alkanediyl;

$R^4$ is hydrogen, $C_{1-6}$alkylsulfonylamino, $C_{3-6}$cycloalkyl, $C_{5-6}$cycloalkanone, Ar-, di(Ar)methyl, Ar-oxy- or $Het^1$;

$R^5$ is hydrogen or $C_{1-6}$alkyl;

$R^6$ is $Het^2$;

$R^7$ is hydrogen, $C_{1-6}$alkyl, hydroxy$C_{1-6}$alkyl, $C_{3-6}$cycloalkyl, Ar or $Het^2$;

X is O, S, $SO_2$ or $NR^8$; said $R^8$ being hydrogen, $C_{1-6}$alkyl or Ar;

$R^9$ is hydrogen, $C_{1-6}$alkyl, $C_{3-6}$cycloalkyl, Ar, $ArC_{1-6}$alkyl, di(Ar)methyl, $C_{1-6}$alkyloxy or hydroxy;

Y is $NR^{10}$ or a direct bond; said $R^{10}$ being hydrogen, $C_{1-6}$alkyl or Ar;

$R^{11}$ and $R^{12}$ each independently are hydrogen, $C_{1-6}$alkyl, $C_{3-6}$cycloalkyl, Ar or $ArC_{1-6}$alkyl, or $R^{11}$ and $R^{12}$ combined with the nitrogen atom bearing $R^{11}$ and $R^{12}$ may form a pyrrolidinyl or piperidinyl ring both being optionally substituted with $C_{1-6}$alkyl, amino or mono or di($C_{1-6}$alkyl)amino, or said $R^{11}$ and $R^{12}$ combined with the nitrogen bearing $R^{11}$ and $R^{12}$ may form a piperazinyl or 4-morpholinyl radical both being optionally substituted with $C_{1-6}$alkyl;

each Ar being unsubstituted phenyl or phenyl substituted with 1, 2 or 3 substituents each independently selected from halo, hydroxy, $C_{1-6}$alkyl, $C_{1-6}$alkyloxy, aminosulfonyl, $C_{1-6}$alkylcarbonyl, nitro, trifluoromethyl, amino or aminocarbonyl; and $Het^1$ and $Het^2$ each independently are selected from furan; furan substituted with $C_{1-6}$alkyl or halo; tetrahydrofuran; a tetrahydrofuran substituted with $C_{1-6}$alkyl; a dioxolane; a dioxolane substituted with $C_{1-6}$alkyl, a dioxane; a dioxane substituted with $C_{1-6}$alkyl; tetrahydropyran; a tetrahydropyran substituted with $C_{1-6}$alkyl; pyrrolidinyl; pyrrolidinyl substituted with one or two substituents each independently selected from halo, hydroxy, cyano, or $C_{1-6}$alkyl; pyridinyl; pyridinyl substituted with one or two substituents each independently selected from halo, hydroxy, cyano, $C_{1-6}$alkyl; pyrimidinyl; pyrimidinyl substituted with one or two substituents each independently selected from halo, hydroxy, cyano, $C_{1-6}$alkyl, $C_{1-6}$alkyloxy, amino and mono and di($C_{1-6}$alkyl)amino; pyridazinyl; pyridazinyl substituted with one or two substituents each independently selected from hydroxy, $C_{1-6}$alkyloxy, $C_{1-6}$alkyl or halo; pyrazinyl; pyrazinyl substituted with one or two substituents each independently selected from halo, hydroxy, cyano, $C_{1-6}$alkyl, $C_{1-6}$alkyloxy, amino, mono- and di($C_{1-6}$alkyl)amino and $C_{1-6}$alkyloxycarbonyl;

$Het^1$ can also be a radical of formula

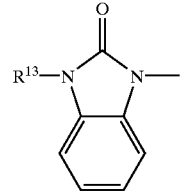 (c-1)

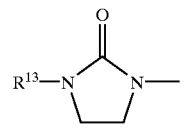 (c-2)

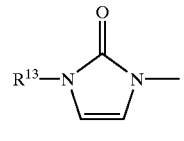 (c-3)

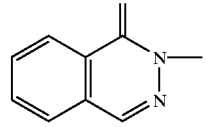 (c-4)

$Het^1$ and $Het^2$ each independently can also be selected from the radicals of formula

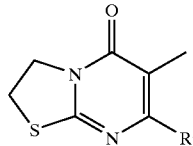 (d-1)

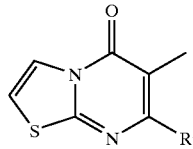 (d-2)

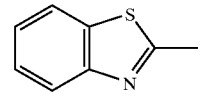 (d-3)

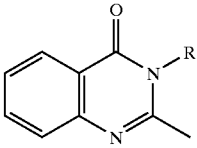 (d-4)

$R^{13}$ and $R^{14}$ each independently are hydrogen or $C_{1-4}$alkyl;

with the proviso that $R^4$ is other than hydrogen, phenyl, 4-fluorophenyl, 4-methylphenyl or 4-methoxyphenyl when $R^1$ and $R^2$ are taken together to form a bivalent radical of formula —O—$CH_2$—$CH_2$—O—; or L is other than n-butyl when $R^1$ and $R^2$ are taken together to form a bivalent radical of formula (a-2) or (a4).

The proviso is intended to exclude compounds E1, E2, E22–E25, E27, E28, E30, E39–E42 which are disclosed in WO-93/05038, compound E6 disclosed in WO-93/16072 and compound FCE 29029A disclosed in WO-96/33186.

As used in the foregoing definitions and hereinafter, halo is generic to fluoro, chloro, bromo and iodo; $C_{1-4}$alkyl defines straight and branched chain saturated hydrocarbon radicals having from 1 to 4 carbon atoms such as, for example, methyl, ethyl, propyl, butyl, 1-methylethyl, 2-methylpropyl and the like; $C_{1-6}$alkyl is meant to include $C_{1-4}$alkyl and the higher homologues thereof having 5 or 6 carbon atoms, such as, for example, 2-methylbutyl, pentyl, hexyl and the like; $C_{2-6}$alkenyl defines straight and branched chain unsaturated hydrocarbon radicals having from 2 to 6 carbon atoms, such as ethenyl, propenyl, butenyl, pentenyl or hexenyl; $C_{2-6}$alkynyl defines straight and branched chain hydrocarbon radicals having from 2 to 6 atoms containing a triple bond, such as ethynyl, propynyl, butynyl, pentynyl or hexynyl; $C_{1-5}$alkanediyl defines bivalent straight and branched chain saturated hydrocarbon radicals having from 1 to 5 carbon atoms such as, for example, methylene, 1,2-ethanediyl, 1,3-propanediyl, 1,4-butanediyl, 1,5-pentanediyl and the like; and $C_{1-6}$alkanediyl is meant to include $C_{1-5}$alkanediyl and the higher homologues thereof having 6 carbon atoms, such as, for example, 1,6-hexanediyl and the like.

The term "stereochemically isomeric forms" as used hereinbefore defines all the possible isomeric forms which the compounds of formula (I) or (I') may possess. Unless otherwise mentioned or indicated, the chemical designation of compounds denotes the mixture of all possible stereochemically isomeric forms, said mixtures containing all diastereomers and enantiomers of the basic molecular structure. More in particular, stereogenic centers may have the R- or S-configuration. Stereochemically isomeric forms of the compounds of formula (I) or (I') are obviously intended to be embraced within the scope of this invention.

Some of the compounds of formula (I) or (I') may also exist in their tautomeric form. Such forms although not explicitly indicated in the above formula are intended to be included within the scope of the present invention. For instance, compounds of formula (I) or (I') wherein $Het^1$ or $Het^2$ is pyrimidinyl substituted with hydroxy, may exist in their corresponding tautomeric form.

The pharmaceutically acceptable acid addition salts as mentioned hereinabove are meant to comprise the therapeutically active non-toxic acid addition salt forms which the compounds of formula (I) or (I') are able to form. The latter can conveniently be obtained by treating the base form with such appropriate acid. Appropriate acids comprise, for example, inorganic acids such as hydrohalic acids, e.g. hydrochloric or hydrobromic acid, sulfuric, nitric, phosphoric and the like acids; or organic acids such as, for example, acetic, propanoic, hydroxyacetic, lactic, pyruvic, oxalic, malonic, succinic (i.e. butanedioic acid), maleic, fumaric, malic, tartaric, citric, methanesulfonic, ethanesulfonic, benzenesulfonic, p-toluenesulfonic, cyclamic, salicylic, p-aminosalicylic, pamoic and the like acids.

Conversely said salt forms can be converted by treatment with an appropriate base into the free base form.

The term addition salt as used hereinabove also comprises the solvates which the compounds of formula (I) or (I') as well as the salts thereof, are able to form. Such solvates are for example hydrates, alcoholates and the like.

The N-oxide forms of the compounds of formula (I) or (I') are meant to comprise those compounds of formula (I) or (I') wherein one or several nitrogen atoms are oxidized to the so-called N-oxide, particularly those N-oxides wherein the piperidine-nitrogen is N-oxidized.

Whenever used hereinafter, the term "compounds of formula (I) or (I')" is meant to also include their N-oxide forms, their pharmaceutically acceptable addition salts, and their stereochemically isomeric forms.

A first interesting group of compounds consists of compounds of formula (I') wherein $R^1$ and $R^2$ are taken together to form a radical of formula (a-2) or (a-3), wherein optionally one or two hydrogen atoms are substituted with methyl; and $R^3$ is halo.

A second group of interesting compounds are those compounds of formula (I') wherein $R^1$ is methoxy, $R^2$ is hydrogen and $R^3$ is chloro.

A particular group of compounds are those compounds of formula (I') wherein L is a radical of formula (b-1) and $R^4$ is $Het^1$ or substituted phenyloxy.

Another particular group of compounds are those compounds formula (I') wherein L is a radical of formula (b-2) or (b-3) and $R^6$ is $Het^2$.

Preferred compounds are those wherein $R^1$ and $R^2$ are taken together to form a radical of formula (a-2) or (a-3), wherein optionally one or two hydrogen atoms are substituted with methyl; $R^3$ is chloro; L is a radical of formula (b-1), (b-2) or (b-3) wherein $R^4$ is substituted phenyloxy, $R^5$ is hydrogen and $R^6$ is $Het^2$; in particular $R^4$ is phenyloxy substituted with halo and $R^6$ is pyrazidinyl or imidazolyl optionally substituted with hydroxy or $C_{1-6}$alkyl.

Most preferred are [1-[2-[(3-methyl-2-pyrazinyl)amino]ethyl]-4-piperidinyl]methyl 4-amino-5-chloro-2,3-dihydro-7-benzofurancarboxylate; or [1-[2-[2,3-dihydro-3-(1-methylethyl)-2-oxo-1H-imidazol-1-yl]ethyl]-4-piperidinyl]-methyl 4-amino-5-chloro-2,3-dihydro-7-benzofurancarboxylate; or [1-[2-[(3-methyl-2-pyrazinyl)amino]ethyl]-4-piperidinyl]methyl 8-amino-7-chloro-2,3-dihydro-1,4-benzodioxin-5-carboxylate; or [1-[1-(3-methyl-2-pyrazinyl)-4-piperidinyl]-4-piperidinyl]methyl 8-amino-7-chloro-2,3-dihydro-1,4-benzodioxin-5-carboxylate; and the pharmaceutically acceptable acid addition salts and the stereo isomeric forms thereof.

The compounds of formula (I') may generally be prepared by reacting an intermediate of formula (II) with a carboxylic acid derivative of formula (III) or a reactive functional derivative thereof, such as, for example, an acid chloride or a carbonyl imidazole derivative. Said esterbond formation may be performed by stirring the reactants in an appropriate solvent in the presence of a base, such as sodium imidazolide.

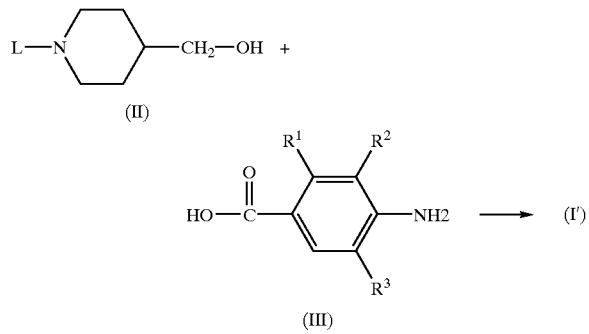

Another way of preparing compounds of formula (I') is by N-alkylating an intermediate of formula (V) with an intermediate of formula (IV), wherein W is an appropriate leaving group such as, for example, a halogen, e.g. chloro or bromo, or a sulfonyloxy leaving group, erg. methanesulfonyloxy or benzenesulfonyloxy.

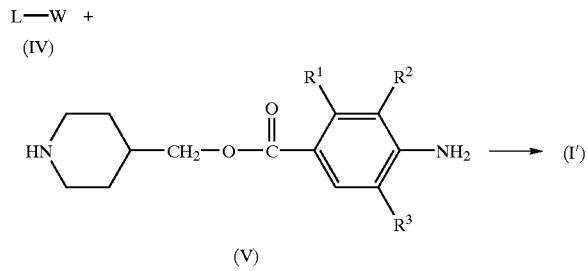

Said N-alkylation reaction can be performed in a reaction-inert solvent such as, for example, a dipolar aprotic solvent, e.g. N,N-dimethylformamide, or a ketone, e.g. methyl isobutylketone, and in the presence of a suitable base such as, for example, sodium carbonate, sodium hydrogen carbonate or triethylamine. Stirring may enhance the rate of the reaction. The reaction may conveniently be carried out at a temperature ranging between room temperature and reflux temperature.

Alternatively, an intermediate of formula (V) is reductively N-alkylated with an intermediate of formula $L'=O$ (IV-a), wherein $L'=O$ represents a derivative of formula L—H wherein two geminal hydrogen atoms are replaced by oxygen, following "art-known reductive N-alkylation procedures".

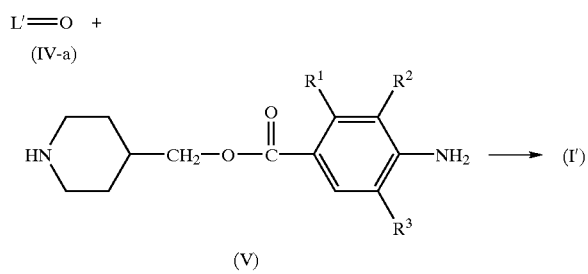

Said reductive N-alkylation may be performed in a reaction-inert solvent such as, for example, dichloromethane, ethanol, toluene or a mixture thereof, and in the presence of a reducing agent such as, for example, a borohydride, e.g. sodium borohydride, sodium cyanoborohydride or triacetoxy borohydride. It may also be convenient to use hydrogen as a reducing agent in combination with a suitable catalyst such as, for example, palladium-on-charcoal or platinum-on-charcoal. In case hydrogen is used as reducing agent, it may be advantageous to add a dehydrating agent to the reaction mixture such as, for example, aluminium tert-butoxide. In order to prevent the undesired further hydrogenation of certain functional groups in the reactants and the reaction products, it may also be advantageous to add an appropriate catalyst-poison to the reaction mixture, e.g., thiophene or quinoline-sulphur. To enhance the rate of the reaction, the temperature may be elevated in a range between room temperature and the reflux temperature of the reaction mixture and optionally the pressure of the hydrogen gas may be raised.

Further, compounds of formula (I') wherein L is Alk'-NHR$^6$ and Alk' is $C_{2-6}$alkanediyl, said compounds being represented by formula (I'-a), can be prepared by treating intermediates (VII) with intermediates (VI), wherein $W^1$ is a suitable leaving group such as, a halo, e.g. chloro, bromo or iodo, or an alkylthio, e.g. methylthio, in an appropriate solvent e.g. acetonitrile or dimethylacetamide.

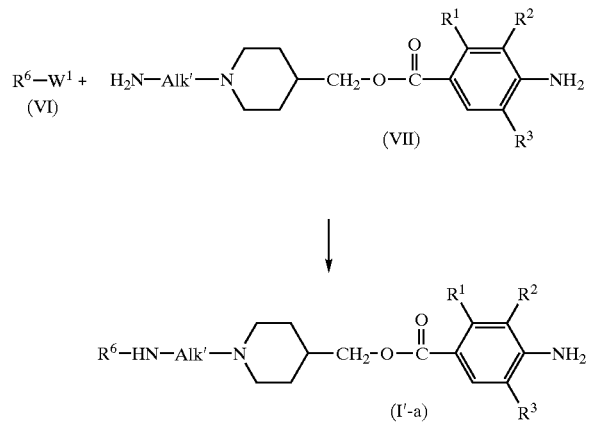

Also, compounds of formula (I') may be prepared by carbonylation of an intermediate of formula (XII), wherein X is bromo or iodo, in the presence of an intermediate of formula (II).

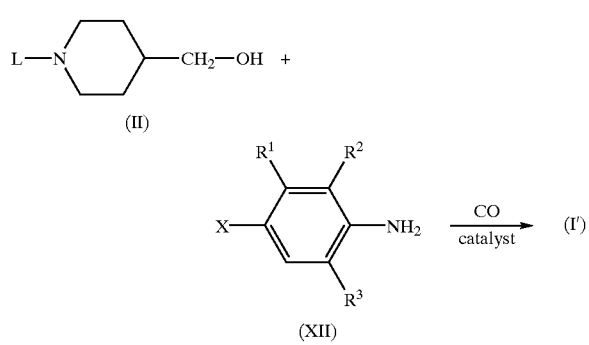

Said carbonylation reaction is carried out in a reaction-inert solvent such as, e.g. acetonitrile or tetrahydrofuran, in the presence of a suitable catalyst and a tertiary amine such as, e.g. triethylamine, and at a temperature ranging between room temperature and the reflux temperature of the reaction mixture. Suitable catalysts are, for instance, palladium-on-carbon, palladium(triphenylphosphine) complexes or Raney nickel. Carbon monoxide is administered at atmospheric pressure or at an increased pressure. Analogous carbonylation reactions are described in Chapter 8 of "Palladium reagents in organic syntheses", Academic Press Ltd., Benchtop Edition 1990, by Richard F. Heck; and the references cited therein.

The compounds of formula (I) may further be prepared by converting compounds of formula (I) into each other according to art-known group transformation reactions.

The compounds of formula (I) may also be converted to the corresponding N-oxide forms following art-known procedures for converting a trivalent nitrogen into its N-oxide form. Said N-oxidation reaction may generally be carried out by reacting the starting material of formula (I) with an appropriate organic or inorganic peroxide. Appropriate inorganic peroxides comprise, for example, hydrogen peroxide, alkali metal or earth alkaline metal peroxides, e.g. sodium peroxide, potassium peroxide; appropriate organic peroxides may comprise peroxy acids such as, for example, benzenecarboperoxoic acid or halo substituted benzenecarboperoxoic acid, e.g. 3-chlorobenzenecarboperoxoic acid, peroxoalkanoic acids, e.g. peroxoacetic acid, alkylhydroperoxides, e.g. tert-butyl hydroperoxide. Suitable solvents are, for example, water, lower alkanols, e.g. ethanol and the like, hydrocarbons, e.g. toluene, ketones, e.g. 2-butanone, halogenated hydrocarbons, e.g. dichloromethane, and mixtures of such solvents.

The starting materials and some of the intermediates are known compounds and are commercially available or may be prepared according to conventional reaction procedures generally known in the art. For instance, some intermediates of formula (III) have been described in EP-0,389,037.

An intermediate of formula (V) may be prepared by reacting an intermediate of formula (VIII), wherein PG represents an appropriate protective group, such as, for example, a tert-butoxycarbonyl, a benzyl group or a photoremovable group, with an acid of formula (III) or an appropriate reactive functional derivative thereof, and subsequent deprotection of the thus formed intermediate, i.e. removal of PG by art-known methods.

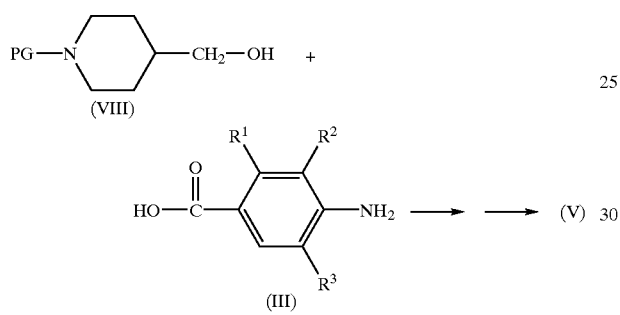

An intermediate of formula (II) may be prepared by reacting an intermediate of formula (IX), which may be prepared by deprotecting an intermediate of formula (VIII), with an intermediate of formula (IV).

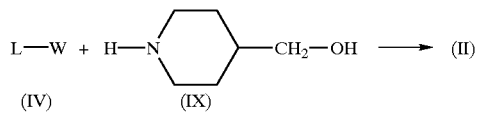

In some cases, it may be appropriate to protect the primary alcohol functionality during the reactionsequence starting from intermediate (IX) to intermediate (II). Protecting groups for primary alcohol functionalities are art-known. These protecting groups may then be removed at the appropriate time during the further synthesis.

Intermediates of formula (VII) can be prepared by treating an intermediate (V) with an intermediate of formula (X), wherein $W^2$ is an appropriate leaving group such as, for example, a halogen, e.g. chloro or bromo, or a sulfonyloxy leaving group, e.g. methane-sulfonyloxy or benzenesulfonyloxy, and Alk'' is $C_{1-5}$alkanediyl, according to the previously described N-alkylation method, and subsequent reduction of intermediate (XI) with an appropriate reducing agent such as, e.g. Raney nickel, in a reaction-inert solvent e.g. THF and in the presence of hydrogen.

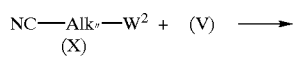

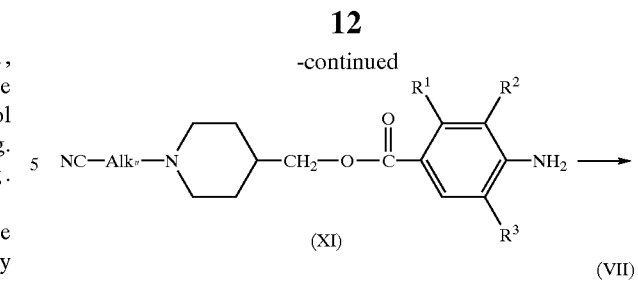

Ester derivatives of intermediates of formula (III) can generally be prepared by carbonylating an intermediate of formula (XII), wherein X is bromo or iodo in the presence of an alcohol of formula (XIV), wherein R is $C_{1-6}$alkyl.

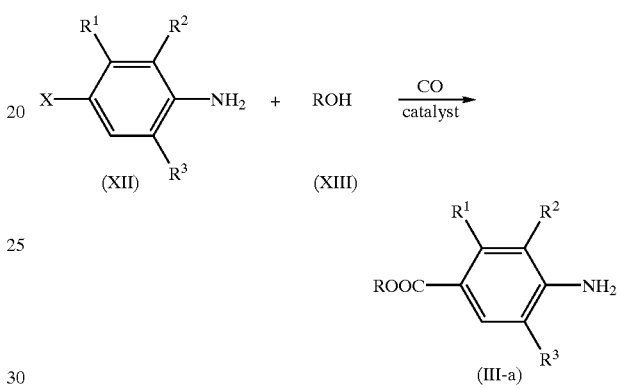

Said carbonylation reaction is carried out in a reaction-inert solvent such as, e.g. acetonitrile or tetrahydrofuran, in the presence of a suitable catalyst and potassium acetate or a tertiary amine such as, e.g. triethylamine, and at a temperature ranging between room temperature and the reflux temperature of the reaction mixture. Suitable catalysts are, for instance, palladium-on-carbon or Raney nickel. Carbon monoxide is administered at atmospheric pressure or at an increased pressure. Analogous carbonylation reactions are described in Chapter 8 of "Palladium reagents in organic syntheses", Academic Press Ltd., Benchtop Edition 1990, by Richard F. Heck; and the references cited therein.

The compounds of formula (I) as prepared in the hereinabove described processes may be synthesized in the form of racemic mixtures of enantiomers which can be separated from one another following art-known resolution procedures. The racemic compounds of formula (I) may be converted into the corresponding diastereomeric salt forms by reaction with a suitable chiral acid. Said diastereomeric salt forms are subsequently separated, for example, by selective or fractional crystallization and the enantiomers are liberated therefrom by alkali. An alternative manner of separating the enantiomeric forms of the compounds of formula (I) involves liquid chromatography using a chiral stationary phase. Said pure stereochemically isomeric forms may also be derived from the corresponding pure stereochemically isomeric forms of the appropriate starting materials, provided that the reaction occurs stereospecifically. Preferably if a specific stereoisomer is desired, said compound will be synthesized by stereospecific methods of preparation. These methods will advantageously employ enantiomerically pure starting materials.

The compounds of formula (I) or (I'), the N-oxide forms, the pharmaceutically acceptable salts and stereoisomeric forms thereof possess favourable intestinal motility stimulating properties. In particular the present compounds show significant gastric emptying activity as is evidenced in example C.1, the "Gastric emptying of an acaloric liquid meal delayed by administration of lidamidine in conscious dogs"-test.

In view of the capability of the compounds of the present invention to enhance the gastrointestinal motility, and in particular to activate gastric emptying, the subject compounds are useful to treat conditions related to a hampered or impaired gastric emptying and more generally to treat conditions related to a hampered or impaired gastrointestinal transit.

The compounds of formula (I) also are believed to have a beneficial effect on the pressure of the LES (Lower Esophagus Sphincter).

Some of the compounds of the present invention also have colon motility stimulating properties.

In view of the utility of the compounds of formula (I), it follows that the present invention also provides a method of treating warm-blooded animals, including humans, (generally called herein patients) suffering from conditions related to a hampered or impaired gastric emptying or more generally suffering from conditions related to a hampered or impaired gastrointestinal transit. Consequently a method of treatment is provided for relieving patients suffering from conditions, such as, for example, gastro-oesophageal reflux, dyspepsia, gastroparesis, constipation, post-operative ileus, and intestinal pseudo-obstruction. Gastroparesis can be brought about by an abnormality in the stomach or as a complication of diseases such as diabetes, progressive systemic sclerosis, anorexia nervosa and myotonic dystrophy. Constipation can result form conditions such as lack of intestinal muscle tone or intestinal spasticity. Post-operative ileus is an obstruction or a kinetic impairment in the intestine due to a disruption in muscle tone following surgery. Intestinal pseudo-obstruction is a condition characterized by constipation, colicky pain, and vomiting, but without evidence of physical obstruction. The compounds of the present invention can thus be used either to take away the actual cause of the condition or to relief the patients from symptoms of the conditions. Dyspepsia is an impairment of the function of digestion, that can arise as a symptom of a primary gastrointestinal dysfunction, especially a gastrointestinal dysfunction related to an increased muscle tone or as a complication due to other disorders such as appendicitis, gallbladder disturbances, or malnutrition.

The symptoms of dyspepsia may also arise due to the intake of chemical substances, e.g. SSRI's.

Hence, the use of a compound of formula (I') as medicine is provided, and in particular the use of a compound of formula (I) for the manufacture of a medicine for treating conditions involving a decreased motility of the stomach. Both prophylactic and therapeutic treatment are envisaged.

To prepare the pharmaceutical compositions of this invention, an effective amount of the particular compound, in base or acid addition salt form, as the active ingredient is combined in intimate admixture with a pharmaceutically acceptable carrier, which carrier may take a wide variety of forms depending on the form of preparation desired for administration. These pharmaceutical compositions are desirably in unitary dosage form suitable, preferably, for administration orally, rectally or by parenteral injection. For example, in preparing the compositions in oral dosage form, any of the usual pharmaceutical media may be employed, such as, for example, water, glycols, oils, alcohols and the like in the case of oral liquid preparations such as suspensions, syrups, elixirs and solutions; or solid carriers such as starches, sugars, kaolin, lubricants, binders, disintegrating agents and the like in the case of powders, pills, capsules and tablets. Because of their ease in administration, tablets and capsules represent the most advantageous oral dosage unit form, in which case solid pharmaceutical carriers are obviously employed. For parenteral compositions, the carrier will usually comprise sterile water, at least in large part, though other ingredients, for example, to aid solubility, may be included. Injectable solutions, for example, may be prepared in which the carrier comprises saline solution, glucose solution or a mixture of saline and glucose solution. Injectable suspensions may also be prepared in which case appropriate liquid carriers, suspending agents and the like may be employed. In the compositions suitable for percutaneous administration, the carrier optionally comprises a penetration enhancing agent and/or a suitable wetting agent, optionally combined with suitable additives of any nature in minor proportions, which additives do not cause a significant deleterious effect to the skin. Said additives may facilitate the administration to the skin and/or may be helpful for preparing the desired compositions.

These compositions may be administered in various ways, e.g., as a transdermal patch, as a spot-on, as an ointment. Acid addition salts of (I) due to their increased water solubility over the corresponding base form, are obviously more suitable in the preparation of aqueous compositions.

It is especially advantageous to formulate the aforementioned pharmaceutical compositions in dosage unit form for ease of administration and uniformity of dosage. Dosage unit form as used in the specification and claims herein refers to physically discrete units suitable as unitary dosages, each unit containing a predetermined quantity of active ingredient calculated to produce the desired therapeutic effect in association with the required pharmaceutical carrier. Examples of such dosage unit forms are tablets (including scored or coated tablets), capsules, pills, powder packets, wafers, injectable solutions or suspensions, teaspoonfuls, tablespoonfuls and the like, and segregated multiples thereof.

In general it is contemplated that a therapeutically effective amount would be from about 0.001 mg/kg to about 10 mg/kg body weight, preferably from about 0.02 mg/kg to about 5 mg/kg body weight. A method of treatment may also include administering the active ingredient on a regimen of between one to four intakes per day.

The following examples are provided for purposes of illustration, not limitation.

Experimental Part

Hereinafter "THF" means tetrahydrofuran, "DIPE" means diisopropylether, "DCM" means dichloromethane, "DMF" means N,N-dimethylformamide and "ACN" means acetonitrile.

A. Preparation of the Intermediates

EXAMPLE A.1

A mixture of 1-(2-amino-ethyl)-4-piperidinemethanol (5.2 g), 2-chloro-3-methyl-pyrazine (5.0 g) and CaO (4.5 g) was stirred for 20 hours at 120° C. The reaction mixture was cooled and purified by column chromatography over silica gel (eluent: $CH_2Cl_2/(CH_3OH/NH_3)$ 92/8). The pure fractions were collected and the solvent was evaporated, yielding 2.3 g (29%) 1-[2-[(3-methyl-2-pyrazinyl)amino]-ethyl]-4-piperidinemethanol (intermediate 1).

EXAMPLE A.2

A mixture of 1-(2-chloroethyl)-1,3-dihydro-3-(1-methylethyl)-2H-imidazol-2-one (12 g), 4-piperidinemethanol hydrochloride (9.1 g), N,N-diethylethanamine (21 ml) and KI (catalytic amount) in DMF (200 ml) was stirred for 20 hours at 70° C. The reaction mixture was cooled and the solvent was evaporated. The residue was purified by column chromatography over silica gel (eluent: $CH_2Cl_2/(CH_3OH/NH_3)$ 95/5). The pure fractions were collected and the solvent was evaporated, yielding 6.9 g (43%) 1,3-dihydro-1-[2-[4-(hydroxymethyl)-1-piperidinyl]ethyl]-3-(1-methylethyl)-2H-imidazol-2-one (intermediate 3).

TABLE 1

L—N(piperidine)—CH$_2$—OH

| Intm. No. | Ex. No. | L | Physical data |
|---|---|---|---|
| 1 | A.1 | pyrazine-NH-(CH$_2$)$_2$- with CH$_3$ | — |
| 2 | A.1 | 3-methylpyrazin-2-yl (piperidinyl with 4-methyl) | mp. 126.7° C. |
| 3 | A.2 | 1-(1-methylethyl)-3-propyl-imidazol-2-one | — |
| 4 | A.2 | 3-(4-fluorophenoxy)propyl | — |
| 5 | A.2 | benzothiazol-2-yl-NH-(CH$_2$)$_2$- | — |
| 6 | A.2 | 1-ethyl-benzimidazol-2(3H)-one-3-(CH$_2$)$_3$- | — |
| 7 | A.2 | phthalazin-1(2H)-one-2-(CH$_2$)$_2$- | — |
| 8 | A.2 | 3-cyanopyridin-2-yl-NH-(CH$_2$)$_3$- | — |
| 9 | A.2 | 3-cyanopyridin-2-yl-NH-(CH$_2$)$_2$- | — |
| 16 | A.2 | 1-butyl-6-chloro-pyridazin-3(2H)-one | — |
| 17 | A.2 | 1-butyl-6-methyl-pyridazin-3(2H)-one | — |

EXAMPLE A.3 a) Sodium hydride (5.8 g) was added to a solution of 1,1-dimethylethyl 1-piperidine-4-methanolcarboxylate (25 g) in THF (800 ml). The mixture was stirred and refluxed for 3 hours (H$_2$ gas evolution), then cooled (solution I). 1,1'-Carbonylbis-1H-imidazole (19.5 g) was added to a suspension of 4-amino-5-chloro-2-methoxybenzoic acid (24 g) in ACN (800 ml), stirred at room temperature. This mixture was stirred for 2 hours at room temperature (solution II). At room temperature, solution (II) was poured out into solution (I) and the reaction mixture was stirred for 20 hours at room temperature. Water (±10 ml) was added. The organic solvent was evaporated. The residue was partitioned between DCM and H$_2$O. The insoluble solid was filtered off. The organic layer was separated, dried, filtered and the solvent was evaporated. The residue was crystallized from ACN (0° C.). The precipitate was filtered off and dried, filtered and the solvent was evaporated. The residue was crystallized from ACN. The precipitate was filtered off and dried (vacuum; 50° C.), yielding 20 g (42%) 1,1-dimethylethyl 4-[[(4-amino-5-chloro-2-methoxy-benzoyl)oxy]methyl]-1-piperidine-carboxylate (intermediate 10).

b) A mixture of intermediate 10 (18 g) in HCl (25 ml) and THF (250 ml) was stirred for 30 minutes at 70° C. The reaction mixture was cooled, alkalized with aqueous ammonia and the layers were separated. The aqueous layer was extracted twice with THF. The combined organic layers were dried, filtered and the solvent was evaporated. The residue was purified by column chromatography over silica gel (eluent: $CH_2Cl_2/(CH_3OH/NH_3)$ 90/10). The pure fractions were collected and the solvent was evaporated. The residue (10 g) was dissolved in CHCl₃, washed with aqueous ammonia, dried, filtered and the solvent was evaporated. The residue was suspended in DIPE, filtered off and dried, yielding 8.5 g (65%) 4-piperidinylmethyl 4-amino-5-chloro-2-methoxybenzoate (intermediate 11).

In a similar way, 4-piperidinylmethyl 4-amino-5-chloro-2,3-dihydro-2,2-dimethyl-7-benzofurancarboxylate (intermediate 12) and 4-piperidinylmethyl 4-amino-5-chloro-2,3-dihydro-7-benzofurancarboxylate(intermediate 13) were synthesized.

EXAMPLE A.4 a) A mixture of chloroacetonitrile (2.15 ml) and (4-piperidinyl)-methyl 8-amino-7-chloro-2,3-dihydro-1,4-benzodioxin-5-carboxylate (11 g) in N,N-diethylethanamine (7 ml) and DMF (150 ml) was stirred at 60° C. until the reaction was complete. Then, the mixture was cooled. The solvent was evaporated. The residue was partitioned between DCM and water. The separated organic layer was dried, filtered and the solvent was evaporated. The residue was crystallized from ACN and the precipitate was filtered off and dried (vacuum, 50° C.), yielding 6.6 g (53%) [1-(cyanomethyl)-4-piperidinyl]-methyl 8-amino-7-chloro-2,3-dihydro-1,4-benzodioxin-5-carboxylate (intermediate 14).

b) A mixture of intermediate 14 (6 g) in THF (250 ml) was hydrogenated with Raney nickel (3 g) as a catalyst. After uptake of hydrogen (2 equivalents), the catalyst was filtered off and the filtrate was evaporated. The residue was purified by column chromatography over silica gel (eluent CH₂Cl₂/(CH₃OH/NH₃) 90/10). The pure fractions were collected and the solvent was evaporated, yielding 4 g (68%) [1-(2-amino-ethyl)-4-piperidinyl]methyl 8-amino-7-chloro-2,3-dihydro-1,4-benzodioxin-5-carboxylate (intermediate 15).

EXAMPLE A.5 a) CaCO₃ (3.9 g) was added to a mixture of 1,3-benzodioxol-4-amine (4.11 g) in DCM (40 ml) and CH₃OH (20 ml). This mixture was stirred at room temperature. N,N,N-trimethyl benzenemethanaminium dichloroiodate (11.5 g) was added portionwise at room temperature. The resulting reaction mixture was stirred for 15 minutes at room temperature. The mixture was diluted with water. The layers were separated. The aqueous phase was extracted with DCM. The combined organic layers were washed with water, dried, filtered and the solvent evaporated. The residue was purified by column chromatography over silica gel (eluent: CH₂Cl₂/hexane 80/20). The pure fractions were collected and the solvent was evaporated. The residue was crystallized from DIPE. The precipitate was filtered off and dried, yielding 3.5 g (46.9%) of 7-iodo-1,3-benzodioxol-4-amine (intermediate 18).

b) Acetic anhydride (14.25 ml) was added dropwise to a mixture of intermediate 18 (36.6 g) in acetic acid (500 ml), stirred at room temperature. The reaction mixture was stirred for 15 minutes at room temperature. The reaction mixture was poured out into water (500 ml). The precipitate was filtered, washed with water, then dried, yielding 39.29 g (92.6%) of N-(7-iodo-1,3-benzodioxol-4-yl)acetamide (intermediate 19).

c) A mixture of intermediate 19 (38.8 g), potassium acetae (20 g) and Pd/C (10%; 2 g) in CH₃OH (500 ml) was stirred at 150° C. under 4.9×10⁶ Pa (50 kg) pressure of CO, during 16 hours. The reaction mixture was cooled, filtered over dicalite, and the filtrate was evaporated. The residue was diluted with water, then extracted three times with DCM. The combined organic layers were dried, filtered and the solvent evaporated. The residue was dissolved in acetic acid (250 ml) and acetic anhydride (6 ml) was added dropwise. The mixture was stirred for 30 minutes at room temperature, then diluted with water (250 ml) and the resulting precipitate was filtered off, washed with water, then dried, yielding 19.4 g (64.7%) of methyl 7-(acetylamino)-1,3-benzodioxole-4-carboxylate (intermediate 20).

d) A mixture of intermediate 20 (18.5 g) and NCS (11.4 g) in ACN (130 ml) was stirred and refluxed for one hour. The reaction mixture was cooled. The precipitate was filtered off, washed with ACN, with DIPE, then dried, yielding 18.2 g (87%) of methyl 7-(acetylamino)-6-chloro-1,3-benzodioxole-4-carboxylate (intermediate 21).

e) Intermediate 21 (18.2 g) was added to a solution of KOH (37.6 g) in water (380 ml). The resulting reaction mixture was stirred and refluxed for 3 hours. The mixture was cooled, acidified with hydrochloric acid, and the resulting precipitate was filtered off, washed with water, suspended in ACN, filtered off, then dried, yielding 14 g (>95%) of 7-amino-6-chloro-1,3-benzodioxole-4-carboxylic acid (intermediate 22).

f) A mixture of intermediate 22 (1 g) and 1,1'-carbonylbis-1H-imidazole (0.8 g) in ACN (80 ml) was stirred for 3 hours at room temperature. The solvent was evaporated. The residue was partitioned between water and DCM. The organic layer was separated, dried, filtered and the solvent was evaporated. The residue was suspended in DIPE, filtered off, then dried (vacuum), yielding 0.8 g (75%) of 1-[(7-amino-6-chloro-1,3-benzodioxol-4-yl)carbonyl]-1H-imidazole (intermediate 23).

B. Preparation of the Final Compounds

EXAMPLE B.1

A mixture of 1-chloro-(4-fluorophenoxy)propane (2.3 g), intermediate 11 (3 g) and N,N-diethylethanamine (2.8 ml) in DMF (50 ml) was stirred for 48 hours at 70° C. The reaction mixture was cooled and the solvent was evaporated. The residue was partitioned between DCM and water. The organic layer was separated, washed with water, dried, filtered and the solvent was evaporated. The residue was purified by column chromatography over silica gel (eluent: CH₂Cl₂/CH₃OH 95/5). The pure fractions were collected and the solvent was evaporated. The residue was crystallized from ACN (0° C.). The precipitate was filtered off and dried (vacuum; 50° C.), yielding 1.17 g (26%) [1-[3-(4-fluorophenoxy)propyl]-4-piperidinyl]methyl 4-amino-5-chloro-2-methoxybenzoate (compound 1, mp. 140.0° C.).

EXAMPLE B.2

Sodium hydride (0.4 g) was added to a solution of intermediate 1 (2.3 g) in THF (65 ml). The mixture was stirred and refluxed for 3 hours, then cooled (solution I). 1,1'-Carbonylbis-1H-imidazole (1.65 g) was added to a solution of 4-amino-5-chloro-2,3-dihydro-2,2-dimethyl-7-benzofurancarboxylic acid (2.42 g) in ACN (65 ml), stirred at room temperature. This mixture was stirred for 2 hours at room temperature. The solvent was evaporated. The residue was dissolved in THF (65 ml) (solution II). At room temperature, solution (II) was poured out into solution (I)

and the reaction mixture was stirred for 90 minutes at room temperature. The solvent was evaporated. The residue was partitioned between DCM and water. The organic layer was separated, dried, filtered and the solvent was evaporated. The residue was purified by column chromatography over silica gel (eluent: CH$_2$Cl$_2$/(CH$_3$OH/NH$_3$) 95/5). The pure fractions were collected and the solvent was evaporated. The residue was solidified in DIPE. The precipitate was filtered off and dried vacuum; 50° C.), yielding 1.58 g (33%) [1-[2-[(3-methyl-2-pyrazinyl)amino]ethyl]-4-piperidinyl]methyl 4-amino-5-chloro-2,3-dihydro-2,2-dimethyl-7-benzofurancarboxylate (compound 6).

EXAMPLE B.3

A mixture of intermediate 15 (2 g) and 4-hydroxy-2-methylthiopyrimidine (0.86 g) in ACN (50 ml) was stirred and refluxed for 24 hours. 4-Hydroxy-2-methylthiopyrimidine (0.28 g) was added. The mixture was stirred and refluxed for 6 hours, cooled and the solvent was evaporated. The residue was taken up in DCM and water. The organic layer was separated, dried, filtered and the solvent was evaporated. The residue was purified by column chromatography over silica gel (eluent: CH$_2$Cl$_2$/CH$_3$OH/(CH$_3$OH/NH$_3$) 88/10/2). The desired fractions were collected and the solvent was evaporated. The residue was repurified by column chromatography over silica gel (eluent: CH$_2$Cl$_2$/(CH$_3$OH/NH$_3$) 90/10). The pure fractions were collected and the solvent was evaporated. The residue was suspended in DIPE, filtered off and dried (vacuum, 60° C.), yielding 0.7 g (27%) [1-[2-[(1,4-dihydro-4-oxo-2-pyrimidinyl)amino]-ethyl]-4-piperidinyl]methyl 8-amino-7-chloro-2,3-dihydro-1,4benzodioxin-5-carboxylate (compound 15).

EXAMPLE B.4

A mixture of intermediate 15 (2 g), 2-chloro-4-hydroxyquinazoline (1.9 g), N,N-dimethylacetamide (0.3 ml) and calciumoxide (0.4 g) was stirred for 1 hour at 140° C., then cooled and partitioned between water and DCM (+methanol). The organic layer was separated, dried, filtered and the solvent was evaporated. The residue was purified by column chromatography over silica gel (eluent: CH$_2$Cl$_2$/(CH$_3$OH/NH$_3$) 95/5). The desired fractions were collected and the solvent was evaporated. The residue was suspended in DIPE, filtered off, then dried (vacuum, 60° C.), yielding 1.4 g (50%) [1-[2-[(1,4-dihydro-4-oxo-2-quinazolinyl)amino]ethyl]-4-piperidinyl]methyl 8-amino-7-chloro-2,3-dihydro-1,4-benzodioxin-5-carboxylate (compound 19).

EXAMPLE B.5

1H-imidazole (2.72 g) was added to a solution of 6-chloro-2-[3-[4-(hydroxymethyl)-1-piperidinyl]propyl]-3(2H)-pyridazinone (2.62 g) in THF (100 ml). NaH (60%, 0.4 g) was added, under nitrogen atmosphere. The mixture was stirred for 10 minutes. 1-[(4-Amino-5-chloro-2,3-dihydro-7-benzofuranyl)carbonyl]-1H-imidazole (2.64 g) was added and the resulting reaction mixture was stirred for 15 minutes at room temperature. The solvent was evaporated. The residue was partitioned between water and DCM. The organic layer was separated, dried, filtered and the solvent was evaporated. The residue was purified by column chromatography over silica gel (eluent: CH$_2$Cl$_2$/hexane/(CH$_3$OH/NH$_3$) 50/45/5). The desired fractions were collected and the solvent was evaporated. The residue was crystallized from DIPE with a drop of ACN. The precipitate was filtered off, washed and dried, yielding 1.88 g (39%) of [1-[3-(3-chloro-6-oxo-1(6H)-pyridazinyl)propyl]-4-piperidinyl]methyl 4-amino-5-chloro-2,3-dihydro-7-benzofurancarboxylate (compound 21, mp: 137° C.) In a similar way, [1-[3-(3-methyl-6-oxo-1(6H)-pyridazinyl)propyl]-4-piperidinyl]-methyl 7-amino-6-chloro-1,3-benzodioxole-4-carboxylate (compound 22) was also prepared.

Tables 2 to 4 list the compounds that were prepared according to one of the above Examples.

TABLE 2

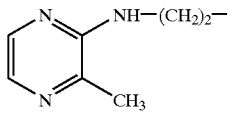

| Co. No. | Ex. No. | L | Physical data |
|---|---|---|---|
| 1 | B.1 | 3-(4-fluorophenoxy)propyl | mp. 140.0° C. |
| 2 | B.2 | 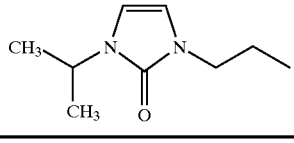 | mp. 103.3° C. |
| 3 | B.2 | 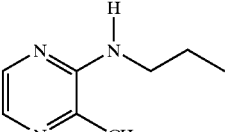 | mp. 130.3° C. |

TABLE 3

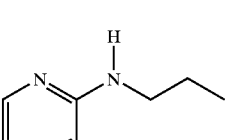

| Co. No. | Ex. No. | L | R$^a$ | Physical data |
|---|---|---|---|---|
| 4 | B.1 | 3-(4-fluorophenoxy)propyl | CH$_3$ | mp. 105.6° C. |
| 5 | B.2 | 3-(4-fluorophenoxy)propyl | H | mp. 130.8° C. |
| 6 | B.2 | ![pyrazinyl-propyl] | CH$_3$ | mp. 126.4° C. |
| 7 | B.2 | ![pyrazinyl-propyl] | H | mp. 188.3° C. |

TABLE 3-continued

[Structure: L-N(piperidine)-CH2-O-C(=O)-[benzofuran with (Rª)2, NH2, Cl substituents]]

| Co. No. | Ex. No. | L | Rª | Physical data |
|---|---|---|---|---|
| 8 | B.2 | [1-isopropyl-3-propyl-imidazol-2(3H)-one] | CH₃ | mp. 78.6° C. |
| 9 | B.2 | [1-isopropyl-3-propyl-imidazol-2(3H)-one] | H | mp. 130.6° C. |
| 20 | B.1 | [2-propyl-6-chloro-pyridazin-3(2H)-one] | H | mp. 178° C. |
| 21 | B.5 | [2-butyl-6-chloro-pyridazin-3(2H)-one] | H | mp. 137° C. |

TABLE 4

[Structure: L-N(piperidine)-CH2-O-C(=O)-[benzene with R¹, R², NH2, Cl]]

| Co. No. | Ex. No. | L | R¹ and R² taken together | Physical data |
|---|---|---|---|---|
| 10 | B.2 | 3-(4-fluorophenoxy)propyl | —O—CH₂—CH₂—O— | mp. 157.1° C.; .C₂H₂O₄ |
| 11 | B.2 | [3-methyl-2-(propylamino)pyrazine] | —O—CH₂CH₂—O— | mp. 121.4° C. |
| 12 | B.2 | [3-methyl-2-(4-methylpiperidin-1-yl)pyrazine] | —O—CH₂CH₂—O— | mp. 168.1° C. |

TABLE 4-continued
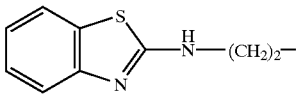
| Co. No. | Ex. No. | L | R¹ and R² taken together | Physical data |
|---|---|---|---|---|
| 13 | B.2 | 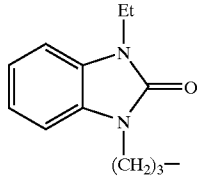 | —O—CH₂CH₂—O— | mp. 168.5° C. |
| 14 | B.2 | 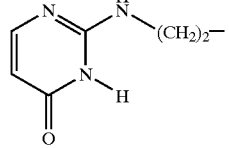 | —O—CH₂CH₂—O— | mp. 138.2° C. |
| 15 | B.3 | 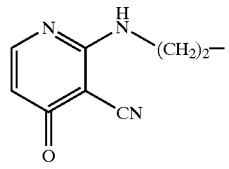 | —O—CH₂CH₂—O— | mp. 130.4° C. |
| 16 | B.2 | 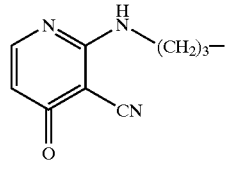 | —O—CH₂CH₂—O— | — |
| 17 | B.2 | 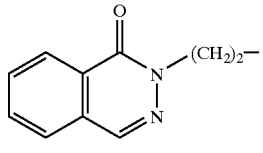 | —O—CH₂CH₂—O— | — |
| 18 | B.2 | 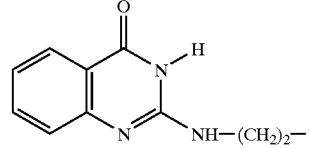 | —O—CH₂—CH₂—O— | mp. 200.4° C.; .C₂H₂O₄ |
| 19 | B.4 | 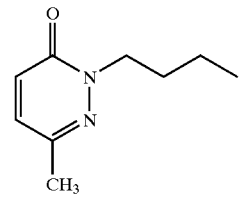 | —O—CH₂CH₂—O— | mp. 145.7° C. |
| 22 | B.5 |  | —O—CH₂—O— | mp. 125° C. |

TABLE 4-continued

[Structure: L—N(piperidine)—CH₂—O—C(=O)—phenyl with R¹, R², NH₂, Cl substituents]

| Co. No. | Ex. No. | L | R¹ and R² taken together | Physical data |
|---|---|---|---|---|
| 23 | B.5 | [1-butyl-6-chloro-pyridazin-3(2H)-one] | —O—CH₂CH₂CH₂—O— | mp. 148° C.; .C₂H₂O₄ |
| 24 | B.5 | [1-propyl-6-chloro-pyridazin-3(2H)-one] | —O—CH₂CH₂—O— | mp. 184° C.; .C₂H₂O₄ |

C. Pharmacological Example

EXAMPLE C.1

"Gastric Emptying of an Acaloric Liquid Test Meal Delayed by Administration of Lidamidine, in Conscious Dogs" Test Female beagle dogs, weighing 7–14 kg, were trained to stand quietly in Pavlov frames. They were implanted with a gastric cannula under general anaesthesia and aseptic precautions. After a median laparatomy, an incision was made through the gastric wall in the longitudinal direction between the greater and the lesser curve, 2 cm above the nerves of Latarjet. The cannula was secured to the gastric wall by means of a double purse string suture and brought out via a stab wound at the left quadrant of the hypochondrium. Dogs were allowed a recovery period of at least two weeks. Experiments were started after a fasting period of 24 hours, during which water was available ad libitum. At the beginning of the experiment, the cannula was opened in order to remove any gastric juice or food remnants.

The stomach was cleansed with 40 to 50 ml lukewarm water. The test compound was administered I.V. (in a volume[2] 3 ml via the vena cephalica), S.C. (in a volume[2] 3 ml) or P.O. (in a volume of 1 ml/kg body weight, applied intragastrically via the cannula with a device that filled the lumen of the cannula; after injection of the test compound, 5 ml NaCl 0.9% was injected in order to correct for the dead space in the injection system). Immediately after administration of the test compound or its solvent, lidamidine 0.63 mg/kg was administered subcutaneously. 30 Minutes later, the cannula was opened to determine the amount of fluid present in the stomach, promptly followed by reintroduction of the fluid. Then the test meal was administered via the cannula. This test meal consisted of 250 ml distilled water containing glucose (5 g/l) as a marker. The cannula remained closed for 30 min, whereafter the gastric contents were drained from the stomach to measure total volume (t=30 minutes). For later analysis 1 ml of the gastric contents was taken, promptly followed by reintroduction of the rest volume into the stomach. This sequence was repeated 4 times with 30 minutes intervals (t=60, 90, 120, 150 minutes).

In the 1 ml samples of the gastric contents, the glucose concentrations were measured on a Hitachi 717 automatic analyser by the hexokinase method (Schmidt, 1961). These data were used to determine the absolute amount of glucose that remained in the stomach after each 30 min period, as a measure for the rest volume of the meal itself, independent of acid secretion.

Curves were fitted to the measurement points (glucose vs time) using weighed non-linear regression analysis. Gastric emptying was quantified as the time needed to empty 70% of the meal ($t_{70\%}$). The control emptying time was calculated as the mean $t_{70\%}$ of the last 5 solvent experiments of the same dog. Acceleration of delayed gastric emptying ($\Delta t$) was calculated as the time difference between $t_{70\%\ compound}$ and $t_{70\%\ solvent}$. To correct for variations in emptying rate between dogs, $\Delta t$ was expressed as % of $t_{70\%\ solvent}$ (Schuurkes et al, 1992).

TABLE 5

Acceleration of gastric emptying of a liquid meal delayed by lidamidine in conscious dog with a dose of 0.04 mg/kg of the test compound.

| Co. No. | Acceleration ($\Delta t/t$) | Co. No. | Acceleration ($\Delta t/t$) |
|---|---|---|---|
| 4 | −0.40 | 11 | −0.54 |
| 6 | −0.41 | 12 | −0.48 |
| 2 | −0.34 | 13 | −0.28 |
| 7 | −0.54 | 10 | −0.30 |
| 3 | −0.30 | 14 | −0.43 |
| 5 | −0.51 | 18 | −0.27 |
| 9 | −0.60 | | |

D. Composition Examples

The following formulations exemplify typical pharmaceutical compositions in dosage unit form suitable for sys-

EXAMPLE D.1
Oral Solutions 9 g of methyl 4-hydroxybenzoate and 1 g of propyl 4-hydroxybenzoate are dissolved in 4 l of boiling purified water. In 3 l of this solution are dissolved first 10 g of 2,3-dihydroxybutanedioic acid and thereafter 20 g of the A.I. The latter solution is combined with the remaining part of the former solution and 12 l of 1,2,3-propanetriol and 3 l of sorbitol 70% solution are added thereto. 40 g of sodium saccharin are dissolved in 0.5 l of water and 2 ml of raspberry and 2 ml of gooseberry essence are added. The latter solution is combined with the former, water is added q.s. to a volume of 20 l providing an oral solution comprising 5 mg of the A.I. per teaspoonful (5 ml). The resulting solution is filled in suitable containers.

EXAMPLE D.2
Capsules 20 g of the A.I., 6 g sodium lauryl sulfate, 56 g starch, 56 g lactose, 0.8 g colloidal silicon dioxide, and 1.2 g magnesium stearate are vigorously stirred together. The resulting mixture is subsequently filled into 1000 suitable hardened gelatin capsules, each comprising 20 mg of the A.I.

EXAMPLE D.3
Film-coated Tablets
Preparation of Tablet Core

A mixture of 100 g of the A.I., 570 g lactose and 200 g starch is mixed well and thereafter humidified with a solution of 5 g sodium dodecyl sulfate and 10 g polyvinylpyrrolidone in about 200 ml of water. The wet powder mixture is sieved, dried and sieved again. Then there are added 100 g microcrystalline cellulose and 15 g hydrogenated vegetable oil. The whole is mixed well and compressed into tablets, giving 10,000 tablets, each comprising 10 mg of the active ingredient.
Coating To a solution of 10 g methyl cellulose in 75 ml of denaturated ethanol there is added a solution of 5 g of ethyl cellulose in 150 ml of dichloromethane. Then there are added 75 ml of dichloromethane and 2.5 ml 1,2,3-propanetriol. 10 g of polyethylene glycol is molten and dissolved in 75 ml of dichloromethane. The latter solution is added to the former and then there are added 2.5 g of magnesium octadecanoate, 5 g of polyvinylpyrrolidone and 30 ml of concen-trated colour suspension and the whole is homogenated. The tablet cores are coated with the thus obtained mixture in a coating apparatus.

EXAMPLE D.4
Injectable Solution 1.8 g methyl 4-hydroxybenzoate and 0.2 g propyl 4-hydroxybenzoate were dissolved in about 0.5 l of boiling water for injection. After cooling to about 50° C. there were added while stirring 4 g lactic acid, 0.05 g propylene glycol and 4 g of the A.I. The solution was cooled to room temperature and supplemented with water for injection q.s. ad 1 l volume, giving a solution of 4 mg/ml of A.I. The solution was sterilized by filtration and filled in sterile containers.

EXAMPLE D.5
Suppositories

3 Grams A.I. was dissolved in a solution of 3 grams 2,3-dihydroxybutanedioic acid in 25 ml polyethylene glycol 400. 12 Grams surfactant and 300 grams triglycerides were molten together. The latter mixture was mixed well with the former solution. The thus obtained mixture was poured into moulds at a temperature of 37–38° C. to form 100 suppositories each containing 30 mg/ml of the A.I.

What is claimed is:

1. A compound of formula

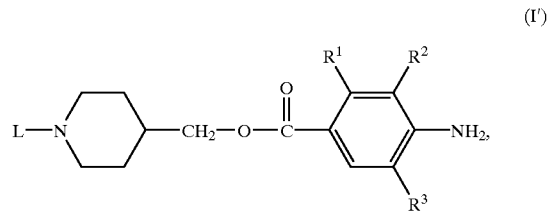

(I')

an N-oxide form, a pharmaceutically acceptable acid addition salt and a stereochemically isomeric form thereof, wherein $R^1$ is $C_{1-6}$ alkyloxy, $C_{2-6}$ alkenyloxy or $C_{2-6}$ alkynyloxy;

$R^2$ is hydrogen or $C_{1-6}$ alkyloxy, or when taken together $R^1$ and $R^2$ may form a bivalent radical of formula

| | |
|---|---|
| —O—CH$_2$—O— | (a-1), |
| —O—CH$_2$—CH$_2$— | (a-2), |
| —O—CH$_2$—CH$_2$—O— | (a-3), |
| —O—CH$_2$—CH$_2$—CH$_2$— | (a-4), |
| —O—CH$_2$—CH$_2$—CH$_2$—O— | (a-5), |
| —O—CH$_2$—CH$_2$—CH$_2$—CH$_2$— | (a-6), | wherein in said bivalent radicals one or two hydrogen atoms may be substituted with $C_{1-6}$alkyl;

$R^3$ is hydrogen or halo

L is a radical of formula

| | |
|---|---|
| -Alk-$R^4$ | (b-1), | wherein
Alk is $C_{1-12}$ alkanediyl;
$R^4$ is Het$^1$;
Het$^1$ is selected from pyridinyl substituted with one or two cyano substituents; pyridazinyl substituted with one or two substituents each independently selected from hydroxy, $C_{1-6}$alkyloxy, $C_{1-6}$alkyl or halo; pyrazinyl substituted with one or two $C_{1-6}$alkyl substituents; Het$^1$ can also be a radical of formula

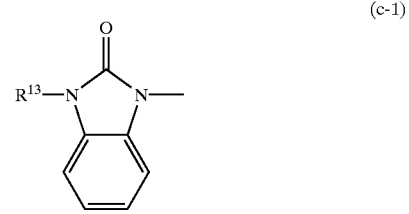

(c-1)

-continued (c-3)
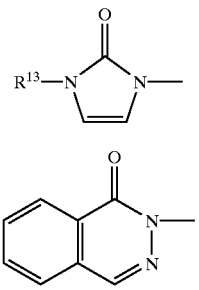

(c-4)
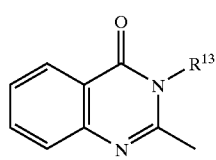

or Het¹ can also be selected from the radicals of formula (d-4)
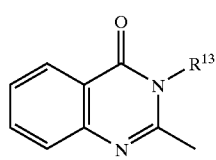

wherein $R^{13}$ is hydrogen or $C_{1-4}$ alkyl.

2. A compound according to claim 1 wherein $R^1$ and $R^2$ are taken together to form a radical of formula (a-2) or (a-3), wherein optionally one or two hydrogen atoms are substituted with methyl; and $R^3$ is halo.

3. A compound according to claim 1 wherein Het¹ is selected from pyrazinyl substituted with one or two $C_{1-6}$ alkyl substituents; the radical of formula (c-1), (c-3) or (c-4).

4. A process for preparing a compound of formula I' as claimed in claim 1 comprising:

a) reacting an intermediate of formula (II) with an carboxylic acid derivative of formula (III) or a reactive functional derivative thereof

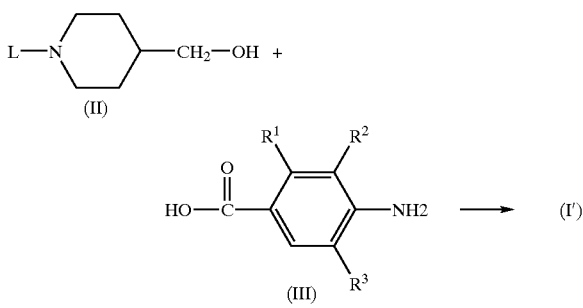

wherein L is as defined in claim 1 or b) N-alkylating an intermediate of formula (IV), wherein W represents a leaving group with a reagent of formula (V); or

L—W +
(IV)

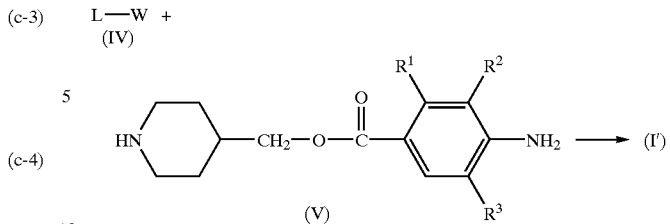

c) reacting a ketone or aldehyde intermediate of formula L'=O(IV-a), said L'=O represents a derivative of formula L—H wherein two geminal hydrogen atoms are replaced by oxygen, with a piperidine of formula (V) or L'=O +
(IV-a)

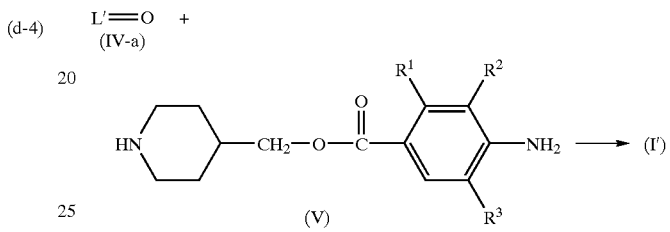

d) carbonylating an intermediate of formula (XII), wherein X is bromo or iodo, in the presence of an intermediate of formula (II)

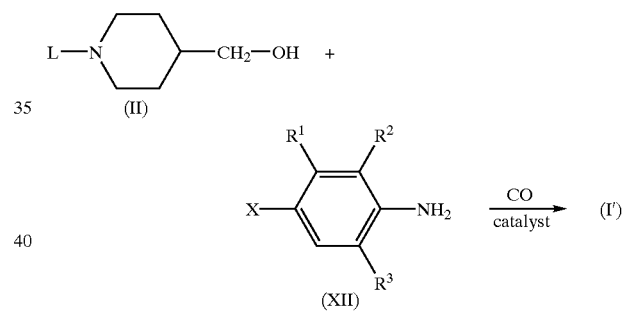

in a reaction-inert solvent in the presence of a catalyst and a tertiary amine and at a temperature ranging between room temperature and the reflux temperature of the reaction mixture.

5. A pharmaceutical composition comprising a pharmaceutically acceptable carrier and a therapeutically active amount of a compound as claimed in claim 1.

6. A method of treating a condition related to a hampered or impaired gastrointestinal transit comprising administering to a host in need thereof an effective amount of a compound of formula (I') as claimed in claim 1.

* * * * *